(12) United States Patent
Kanazirev et al.

(10) Patent No.: US 9,517,447 B1
(45) Date of Patent: Dec. 13, 2016

(54) PROCESSES FOR REMOVING CONTAMINANTS FROM A DEHYDROGENATION EFFLUENT

(71) Applicant: UOP LLC, Des Plaines, IL (US)

(72) Inventors: Vladislav I. Kanazirev, Arlington Heights, IL (US); Jayant K. Gorawara, Buffalo Grove, IL (US); Joseph E. Zimmermann, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 10 days.

(21) Appl. No.: 14/727,246

(22) Filed: Jun. 1, 2015

(51) Int. Cl.
*C07C 5/327* (2006.01)
*C07C 5/333* (2006.01)
*C07C 7/12* (2006.01)
*B01J 20/34* (2006.01)

(52) U.S. Cl.
CPC ............ *B01J 20/3458* (2013.01); *C07C 5/333* (2013.01); *C07C 7/12* (2013.01)

(58) Field of Classification Search
CPC ............. C07C 5/327; C07C 5/333; C07C 7/12
USPC ........... 585/654, 655, 820, 822, 823; 502/34
See application file for complete search history.

(56) References Cited

U.S. PATENT DOCUMENTS

| | | | |
|---|---|---|---|
| 3,898,153 A | 8/1975 | Louder et al. | |
| 4,374,654 A | 2/1983 | McCoy | |
| 7,956,006 B2 | 6/2011 | Gangwal et al. | |
| 8,889,089 B2 | 11/2014 | Aasberg-Petersen et al. | |
| 2014/0378725 A1* | 12/2014 | Luebke | C07C 7/12 585/324 |

FOREIGN PATENT DOCUMENTS

EP   0 539 433 B1   7/1996

OTHER PUBLICATIONS

Park et al., "Simultaneous removal of H2S and COS using Zn-based solid sorbents . . . ," Korean Journal of Chemical Engineering (2012), 29(12), 1812-1816.
Brown et al., "New chloride removal catalyst in CCR unit", NPRA Annual Meeting Papers (2001), vol. 2001, New Orleans, LA, 10 pages.

\* cited by examiner

*Primary Examiner* — Thuan D Dang

(57) ABSTRACT

A process for the providing a regenerant gas stream for a regenerable adsorbent used to remove water and hydrogen sulfide from a reactor effluent in a catalytic dehydrogenation process is described. The reactor effluent is compressed in a compressor to provide a compressed effluent. The compressed effluent may be treated to remove chlorides, and then passed to a dryer zone having a regenerable adsorbent. A regenerant gas stream is used to desorb the water and hydrogen sulfide and the spent regenerant stream may be passed to a cleaning zone having a sorbent configured to remove hydrogen sulfide from the spent regenerant stream. The cleaned regenerant gas stream may be recycled to the dryer zone to desorb and/or regenerate the regenerable adsorbent.

7 Claims, 1 Drawing Sheet

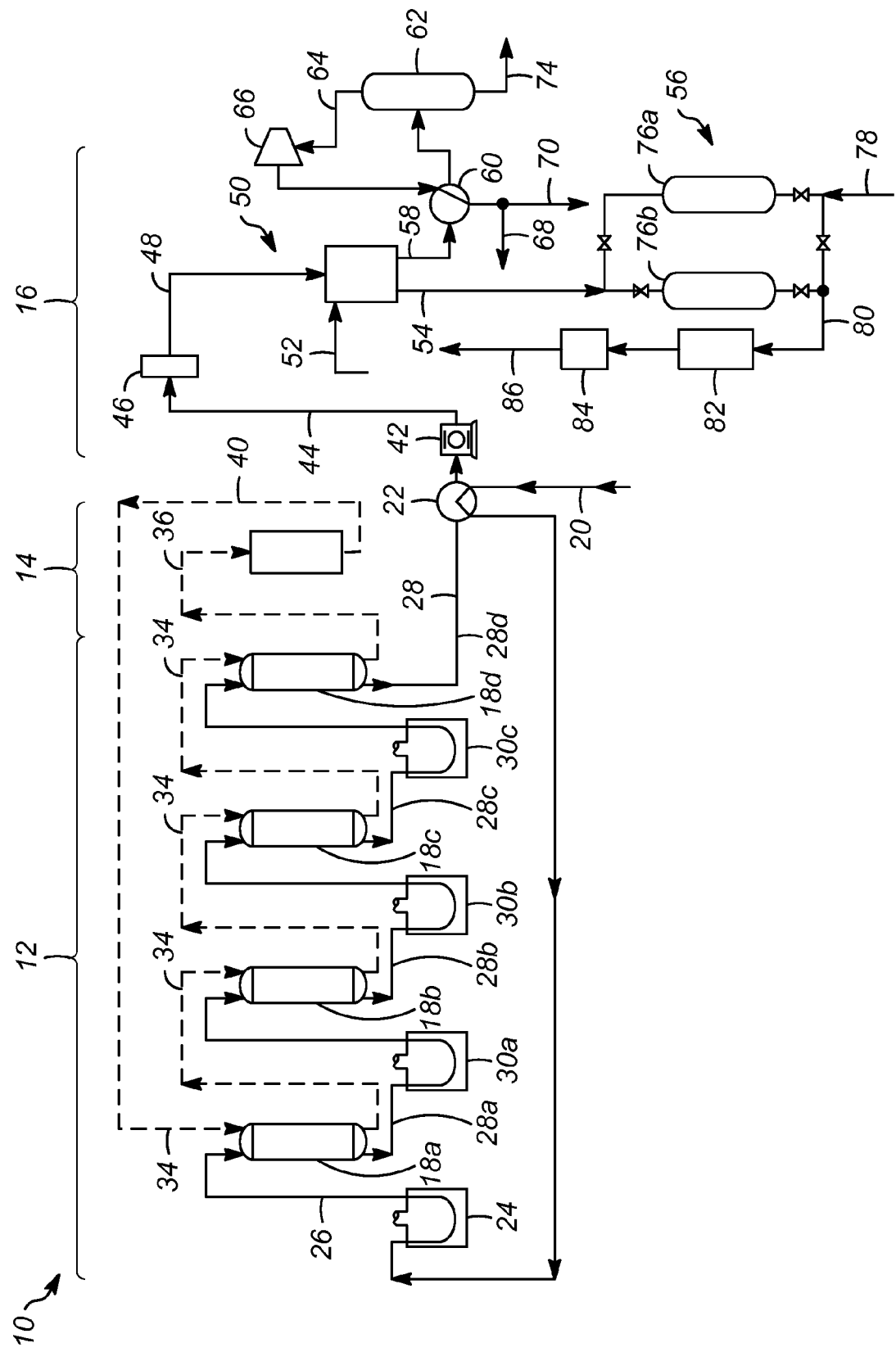

PROCESSES FOR REMOVING CONTAMINANTS FROM A DEHYDROGENATION EFFLUENT

FIELD OF THE INVENTION

This invention relates generally to processes for removing contaminants from a dehydrogenation effluent, and more particularly to processes for removing sulfur compounds from same, and even more particularly to processes for treating a regenerant gas used with an adsorbent used to remove sulfur compounds.

BACKGROUND OF THE INVENTION

Catalytic dehydrogenation can be used to convert paraffins to the corresponding olefin, e.g., propane to propene, or butane to butene. U.S. Pat. No. 5,481,060 discloses an exemplary dehydrogenation process. In a typical arrangement for a catalytic dehydrogenation, the process includes a reactor section, a catalyst regeneration section, and a product recovery section. The product recovery system includes various zones to remove one or more contaminants from an effluent from the reaction section.

For example, the effluent from the reactor section typically passes through a chloride removal section. After chloride removal, the treated effluent is passed to a reactor effluent dryer system (RED) for drying and further purification, including removal of water and hydrogen sulfide ($H_2S$). An exemplary reactor effluent dryer (RED) system includes two or more adsorbent beds arranged in a typical thermal swing adsorption (TSA) system.

As is known, in a TSA, while one or more adsorbent beds is operated in adsorption mode to purify and dehydrate the process stream, the other bed(s) are operated in regeneration mode. When the adsorbent bed(s) in the adsorption step starts to breakthrough the contaminants, the bed(s) on adsorbent mode is switched to regeneration mode and the freshly regenerated bed(s) are placed in adsorption mode. The beds are switched between adsorption and regeneration modes to provide for continuous purification of the process stream. Regeneration of the adsorbents is accomplished by purging the beds with a regenerant stream such as an inert gas, net gas, or vaporized hydrocarbon stream, at elevated temperature to desorb the impurities and water to rejuvenate or regenerate the adsorbent and prepare it for a fresh adsorption step. The TSA process is well known to those skilled in the art.

After desorbing and/or regenerating the regenerable adsorbed in the RED, the spent regenerant gas is typically cooled down and passed to a collection drum to remove heavier hydrocarbons (formed in the reactor through side reactions), such as polynuclear aromatics. The cooled gas is then passed into a regenerant gas scrubber, and, after being cleaned, depending on the composition of the regenerant gas, the regenerant gas may be used as fuel gas.

The regenerant gas scrubber typically contains circulating caustic solution (sodium hydroxide (NaOH)) in which the hydrogen sulfide ($H_2S$) is converted into sodium sulfide ($Na_2S$) and sodium bisulfide (NaHS). Both of these sulfide compounds are toxic and presents environmental problems. In addition, the caustic solution is considered spent at approximately 70% utilization. The disposal of the spent caustic solution is costly and creates handling problems. Furthermore, since the caustic solution has to be continuously replaced, the operating costs associated with constantly supplying caustic and disposing of same can be very large. The use of solid potassium hydroxide (KOH) pellets placed in a vessel may not address these problem because of operational difficulties associated with the solid particles, and the continue problems associated with spent material disposal.

Alternatively, it is known to treat regenerant gas in a sulfur recovery unit (SRU) which utilizes the Claus catalytic process which converts hydrogen sulfide to elemental sulfur. This treatment of the regenerant gas without utilizing caustic is possible for large facilities processing hydrogen sulfide containing waste streams from different units. However, the dehydrogenation units are typically part of a petrochemical complexes which rarely have an SRU. Thus, the petrochemical complexes typically resort to utilizing caustic.

Therefore, there remains a need for an effective and efficient process for treating a spent regenerant gas that does not utilize a caustic solution or solid hydroxide salt pellets and that does not require an SRU. It would also be desirable to have such a process that allows for the regenerant gas to be recycled instead of being used as fuel gas.

SUMMARY OF THE INVENTION

One or more processes have been invented in which a solid adsorbent is used to remove sulfide compounds from the spent regenerant gas stream.

In a first aspect of the present invention, the present invention may be broadly characterized as providing a process for producing a reusable regenerant gas stream by: compressing a reactor effluent from a catalyst dehydrogenation process to provide a compressed effluent; removing chlorides from the compressed effluent in a chloride removal zone to provide a treated effluent; removing water and hydrogen sulfide from the treated effluent in a dryer zone to provide a dryer output stream, the dryer zone having at least one vessel comprising a regenerable adsorbent; regenerating the regenerable adsorbent in the dryer zone with a regenerant gas stream to provide a spent regenerant gas stream, the spent regenerant stream including water and hydrogen sulfide; and, removing the hydrogen sulfide from the spent regenerant gas stream in a regenerant cleaning zone to provide a cleaned regenerant stream, the regenerant cleaning zone including one or more vessels having a sorbent configured to remove hydrogen sulfide from the spent regenerant gas.

In various embodiments of the present invention, regenerating the regenerable adsorbent further comprises cooling the regenerable adsorbent. It is contemplated that the regenerable adsorbent is cooled with the cleaned regenerant stream.

In some embodiments of the present invention, the process further includes cooling the cleaned regenerant stream to provide a cooled regenerant stream. It is contemplated that the process also includes removing contaminants from the cooled regenerant stream. It is further contemplated that the contaminants are removed from the regenerant stream by cooling. It is also contemplated that the process includes recycling the cooled regenerant stream to the dryer zone as the regenerant gas stream.

In at least one embodiment of the present invention, the regenerant cleaning zone comprises at least two vessels.

In one or more embodiments of the present invention, the regenerant cleaning zone comprises two vessels operated in a lead-lag configuration. It is contemplated that at least one vessel is used as a heat exchanger to provide heat or remove heat from a stream of gas including regenerant. It is further contemplated that the heat exchanger cools the cleaned regenerant stream to provide a cooled regenerant stream.

In a second aspect of the present invention, the present invention may be broadly characterized as providing a process for removing contaminants from a reactor effluent of a catalyst dehydrogenation process by: dehydrogenating a hydrocarbon feed in a dehydrogenation reaction zone under dehydrogenation reaction conditions in the presence of a dehydrogenation catalyst to form a reactor effluent; compressing the reactor effluent to provide a compressed effluent; removing chloride contaminants from the compressed effluent in a chloride removal zone to provide a treated effluent; removing water and hydrogen sulfide from the treated effluent in a dryer zone to provide a dryer output stream including olefins and unconverted paraffins, the dryer zone having at least one vessel comprising a regenerable adsorbent; regenerating the regenerable adsorbent in the dryer zone with a regenerant gas stream to provide a spent regenerant stream, the spent regenerant stream including water and hydrogen sulfide; and, removing the hydrogen sulfide from the spent regenerant stream in a regenerant cleaning zone to provide a cleaned regenerant stream, the regenerant cleaning zone including one or more vessels having a sorbent configured to remove hydrogen sulfide from the spent regenerant gas.

In various embodiments of the present invention, the process includes separating the dryer output stream in a product separator into a vapor stream and a liquid stream, the liquid stream comprising an olefin product stream. It is contemplated that the regenerant gas stream comprises a portion of the reactor effluent. It is also contemplated that the dehydrogenation reaction zone comprises a plurality of reactors, and wherein the regenerant gas stream comprises an effluent stream. It is contemplated that the process further includes compressing the cleaned regenerant gas stream to provide a compressed regenerant gas; and passing the compressed regenerant gas to a water removal vessel to remove water, heavy hydrocarbons, or both from the compressed regenerant gas. It is also contemplated that the process further includes passing the compressed regenerant gas to the product separator. It is further contemplated that the process also includes combining the compressed regenerant gas with the compressed effluent. It is contemplated that the process also includes combining the compressed regenerant gas with the treated effluent.

In some embodiments of the present invention, the sorbent in the regenerant cleaning zone comprises a solid adsorbent including a metal oxide on a support.

In one or more embodiments of the present invention, the regenerant cleaning zone comprises at least two vessels arranged in a lead-lag configuration.

In a third aspect of the present invention, the present invention maybe broadly characterized as providing a process for cleaning a regenerant stream by: regenerating a regenerable adsorbent with a regenerant gas stream to provide a spent regenerant stream, the spent regenerant stream including water and hydrogen sulfide; removing the hydrogen sulfide from the spent regenerant stream in a regenerant cleaning zone to provide a cleaned regenerant stream, the regenerant cleaning zone including one or more vessels having a solid adsorbent including a metal oxide on a support configured to selectively immobilize hydrogen sulfide; and, regenerating a regenerable adsorbent with at least a portion of the cleaned regenerant stream.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing FIGURE, in which:

The FIGURE depicts a process flow diagram of an exemplary process according to one or more embodiments of the present invention.

DETAILED DESCRIPTION OF THE INVENTION

As mentioned above, various processes have been invented in which a solid adsorbent is used to remove sulfide compounds from the spent regenerant gas stream. The use of the adsorbent addresses the environmental concerns because some adsorbents can be recycled or at least more easily disposed compared to the caustic solution or solid hydroxide pellets. Additionally, the cost of supplying and disposing of the adsorbent is believed to be considerably less than the same costs associated with the caustic solution or solid hydroxide pellets. Finally, some of the processes provide for the recycling of a cleaned regenerant gas to the dryer section as opposed to being used as a fuel gas.

With these general principles in mind, one or more embodiments of the present invention will be described with the understanding that the following description is not intended to be limiting.

While the present invention will be described in relation to a catalytic dehydrogenation process, it is believed that the processes of treating a regenerant gas stream are applicable to many additional processes, including other processes for the dehydrogenation. The present invention is applicable in any of such processes in which the reaction effluent includes a hydrogen sulfide. As shown in the FIGURE, a typical arrangement for a catalytic dehydrogenation unit 10 is shown. The catalytic dehydrogenation unit 10 includes a reactor section 12, a catalyst regeneration section 14, and a product recovery section 16. The reactor section 12 may include one or more reactors 18a, 18b, 18c, 18d. As shown in the FIGURE, four reactors 18a, 18b, 18c, 18d are included in the reactor section 12. This is merely a preferred arrangement.

In an exemplary embodiment, a hydrocarbon feed 20 including hydrocarbons and hydrogen is initially heated in a heat exchanger 22 via indirect heat exchange with a reactor effluent (discussion below) from the reactor section 12. Following heating, the hydrocarbon feed 20 normally passes through a preheater 24 to further increase the temperature of the feed components to form a preheated feed 26 before it enters the reactors 18a, 18b, 18c, 18d where it is contacted with the dehydrogenation catalyst.

Since the dehydrogenation reaction is endothermic, the temperature of a dehydrogenation effluent 28a from the first reactor 18a is less than the temperature of the preheated feed 26. Accordingly, before being passed to a second reactor 18b, the dehydrogenation effluent 28a from the first reactor 18a may be passed to an interstage heater 30a to raise the temperature to a desired inlet temperature for the second reactor 18b.

Similarly, the second reactor 18b will produce a second dehydrogenation effluent 28b which may be passed to an interstage heater 30b, to raise the temperature to a desired inlet temperature for a third reactor 18c. Likewise, the third reactor 18c will provide a third dehydrogenation effluent 28c which may be passed to an interstage heater 30c, to raise the temperature to a desired inlet temperature for a fourth reactor 18d. As will be appreciated, the number of reactors can be different than the depicted embodiment. After the last reactor (in this example, the fourth reactor 18d), a reactor effluent 28b, comprising a net reactor effluent 28, may be passed to the heat exchanger 22 to allow for heat to be exchanged with the hydrocarbon feed 20 (discussed above). The net reactor effluent 28 may then be passed to the product recovery section 16 (discussed in more detail below).

The dehydrogenation reaction is a highly endothermic reaction which is typically effected at low (near atmospheric) pressure conditions. The precise dehydrogenation temperature and pressure employed in the dehydrogenation reaction zone will depend on a variety of factors, such as the composition of the paraffinic hydrocarbon feedstock, the activity of the selected catalyst, and the hydrocarbon conversion rate. In general, dehydrogenation conditions include a pressure of from about 0 MPa (0 bar) to about 3.5 MPa (35 bars) and a temperature of from about 480° C. (900° F.) to about 760° C. (1400° F.).

The hydrocarbon feed 20 is typically charged to the reactors 18a, 18b, 18c, 18d and contacted with the catalyst contained therein at an LHSV of from about 1 to about 10. Hydrogen, principally recycle hydrogen, is suitably admixed with the hydrocarbon feed 30 in a mole ratio of from about 0.1 to about 10. Preferred dehydrogenation conditions, particularly with respect to $C_3$-$C_5$ paraffinic hydrocarbon feedstocks, include a pressure of from about 0 MPa (0 bar) to about 0.5 MPa (5 bars) and a temperature of from about 540° C. (1000° F.) to about 705° C. (1300° F.), a hydrogen-to-hydrocarbon mole ratio of from about 0.1 to about 2, and an LHSV of less than 4.

The dehydrogenation reaction may utilize a catalyst 34 which moves through the series of reactors 18a, 18b, 18c, 18d. A spent catalyst 36 may be passed from the last reactor 18d to the catalyst regeneration section 14. The catalyst regeneration section 14 typically includes a reactor 38 where coke on the spent catalyst 36 is burned off and the catalyst may go through a reconditioning step. A regenerated catalyst 40 may be sent back to the first reactor 18a as the catalyst 34. Additionally, fresh catalyst may also be added (not shown).

The dehydrogenation may use any suitable dehydrogenation catalyst. Generally, preferred suitable catalyst comprises a Group VIII noble metal component (e.g., platinum, iridium, rhodium, and palladium), an alkali metal component, and a porous inorganic carrier material. The catalyst may also contain promoter metals which advantageously improve the performance of the catalyst. The porous carrier material should be relatively refractory to the conditions utilized in the reactor section 12 and may be chosen from those carrier materials which have traditionally been utilized in dual function hydrocarbon conversion catalysts. A preferred porous carrier material is a refractory inorganic oxide, with the most preferred an alumina carrier material. The particles are usually spheroidal and have a diameter of from about 1.6 to about 3.2 mm (about 1/16 to about 1/8 inch), although they may be as large as about 6.4 mm (about 1/4 inch).

Operation of the reactor section 12 will produce a mixture of hydrogen and hydrocarbons. Normally, a portion of the hydrocarbons will include an equilibrium mixture of the desired olefin and its alkane precursor. The reactor effluent 28 from the reactor section 12 passes to the product recovery section 16. As will be discussed in more detail below, the product recovery section 16 removes hydrogen from the reactor effluent 28 and may recover it in high purity for recycle to the reactor section 12. Separation steps for the removal of hydrogen will normally include cooling and compressing with subsequent cooling and flashing in a separation vessel. Such methods for the separation of hydrogen and light gases are well known by those skilled in the art.

In the product recovery section 16, the net reactor effluent 28 is compressed in a compressor 42 to provide a compressed effluent 44. The compressed effluent 44 may be introduced directly into a chloride removal zone 46, as shown, or may be passed through a cooler or heater to adjust the temperature of the compressed effluent 44, to a temperature that is above the dew point temperature of the compressed effluent stream 44 at the particular process conditions. In an example embodiment, the temperature of the chloride removal zone 46 is between about 75 to 250° C. (about 167 to 482° F.), more preferably between about 75 to 177° C. (about 167 to about 351° F.), and most preferably between about 93 to 157° C. (about 199 to 315° F.).

As will be appreciated by those of ordinary skill in the art, the use of organic chloride used to condition paraffin dehydrogenation catalysts typically results in undesirable chlorinated species (chloride) compounds, such as hydrochloric acid (HCl) and organic chlorides (RCl), in the net reactor effluent 28. Such compounds are referred to herein as trace chloride contaminants. Example deleterious effects from untreated trace chloride contaminants include corrosion, poisoning of downstream catalysts, and other effects. Accordingly, the product recovery section 16 in typical catalytic dehydrogenation unit includes a process for removal of trace chloride contaminants.

In the chloride removal zone 46, chloride present in the compressed effluent 44 is adsorbed with an adsorbent to provide a treated effluent 48. An exemplary chloride removal zone 46 is discussed in more detail in U.S. Pat. No. 2014/0378725, the entirety of which is incorporated herein by reference. The treated effluent 48 may then be passed to a dryer zone 50.

The dryer zone 50 may be a reactor effluent dryer system (RED) for drying and purification, including water and hydrogen sulfide ($H_2S$) removal. An example reactor effluent dryer (RED) system includes two or more adsorbent vessels arranged in a typical thermal swing adsorption (TSA) system. While one or more adsorbent vessels is in adsorption mode to purify and dehydrate the process stream, the other vessel(s) are in regeneration mode. When the adsorbent vessel(s) in the adsorption step starts to break through the contaminants, the vessel(s) on adsorbent mode is switched to regeneration mode and the freshly regenerated vessel (s) are placed in adsorption mode. The vessels are switched between adsorption and regeneration modes to provide for continuous purification of the treated effluent 48. The TSA process is well known to those skilled in the art.

Desorption of the hydrogen sulfide and regeneration of the adsorbents is accomplished by purging the beds with a regenerant gas stream 52 such as an inert gas, net gas, or vaporized hydrocarbon stream, at elevated temperature to desorb the impurities and water to rejuvenate the adsorbent and prepare it for a fresh adsorption step. A spent regenerant gas 54, including the impurities removed from the adsorbents, is passed to a regenerant cleaning zone 56 (discussed in more detail below).

From the dryer zone 50, a dryer output stream 58 may be heated in a heat exchanger 60 and then separated in a product separator 62. A gas stream 64 from the product separator 62 may be expanded in expander 66. After exchanging heat in the heat exchanger 60 with the dryer output stream 58, the vapor stream from the expander 66 may be and separated into a recycle hydrogen stream 68 and a net separator gas stream 70. The recycle hydrogen stream 68 may be combined with the hydrocarbon feed 20.

A liquid stream 74, which includes the olefin product and unconverted paraffin, from the product separator 62 may be sent for further processing, where the desired olefin product is recovered and the unconverted paraffin is recycled to the reactor section 12.

Returning to the dryer zone 50, as discussed above, in contrast to the prior art processes in which a caustic solution, solid hydroxide salt, or an SRU is used to clean the spent regenerant gas 54, in the processes of the present invention, the regenerant cleaning zone 56 includes one or more vessels 76a, 76b each having a sorbent configured to remove hydrogen sulfide from the spent regenerant gas 54, preferably by immobilizing hydrogen sulfide.

The spent regenerant gas 54 may be introduced, after exiting the dryer zone 50, to the regenerant cleaning zone 56 comprising, in an embodiment, two fixed bed vessels 76a, 76b operated in lead-lag configuration. The vessels 76a, 76b serve also as heat exchangers to provide for a regenerant gas stream with a reduced or lower temperature that can be utilized during the regeneration operation of the dryer zone 50. For example, in regenerant heater operation, the duration of the regeneration/cooling cycles can be adjusted to keep a certain temperature profile in the regenerant cleaning zone 56. The regenerated adsorbent bed in the vessels 76a, 76b may be still cooled down by fresh regenerant 78 which passes into the regenerant cleaning zone 56 through the vessels 76a, 76b or by a cleaned regenerant stream 80 that has been cooled.

It is desired that the adsorbent is capable of operating at high temperatures similar to these applied to RED regeneration. In addition, the adsorbent preferably has a high sulfur capacity and, most preferably also a low reactivity and ability to handle the contaminants present in the spent regenerant, mostly hydrogen sulfide ($H_2S$) and carbonyl sulfide (COS), to a very low residual concentration. The sulfur capacity of the adsorbent at the typical regeneration temperatures of the RED beds may exceeds 200 Kg/m$^3$ without any detrimental effects on the hydrocarbon feed.

The sorbent may comprise a zinc oxide (ZnO) containing composite adsorbent, GB-280, available from UOP LLC of Des Plaines, Ill., is an example of the sorbent suitable for this invention. As will be appreciated, the sulfur containing compounds will chemically react with the metal in the adsorbent to form metal sulfide. Additionally, all of the carbonyl sulfide may be fully converted by the metal on the adsorbent. The spent sorbent is preferably not hazardous and can be recycled. It is also contemplated that the adsorbents comprises another high capacity metal absorbents, such as manganese or iron. Preferably, the sorbent comprises porous shaped particles with a median particle size of between 0.5-12 mm.

The contacting of the sorbent and the spent regenerant gas 54 can be carried out in a batch or continuous process. The sorbent can be present as a fixed bed, moving bed or radial flow bed and may have a bulk density between 200-2000 kg/m$^3$. When a fixed bed is used, the spent regenerant gas 54 can be flowed in an upflow or downflow direction, with upflow being generally preferred for liquid feeds. If a moving bed is used the spent regenerant gas 54 flow can be either co-current or counter-current. Further, when a fixed bed is used, multiple beds can be used and can be placed in one or more reactor vessel. Adsorption conditions generally include a temperature of about ambient to about 80° C. (176° F.), a pressure of about atmospheric to about 10,132 kPa (1,470 psi) and a contact time in which the gas hourly space velocity varies from about 500 to about 10,000 hr$^{-1}$. In some embodiments, the temperature may be between 250 to 290° C. (482 to 554° F.). Furthermore, the concentration of hydrogen sulfide in the spent regenerant gas 54 may be between 1 to 10,000 ppm, and will most likely vary within that range throughout the process. As will be appreciated these conditions are merely exemplary.

After a certain amount of time, which time depends on the concentration of contaminants, the size of the bed and the space velocity, the sorbent will be substantially spent, i.e. has adsorbed an amount of contaminant(s) such that the level of contaminant in the purified stream is above an acceptable level. At this time, the sorbent is removed and replaced with fresh sorbent. The spent sorbent can be regenerated by means well known in the art and then placed back on service.

The lead-lag bed configuration of the regenerant cleaning zone 56 is merely a preferred embodiment whereas the lag vessel would have sufficient residual sulfur capacity while the lead vessel may be cooled down and re-charged with fresh adsorbent. The removed spent adsorbent may be recycled or otherwise disposed of.

The cleaned regenerant stream 80 or stream including some fresh regenerant 78, may be passed a hydrocarbon removal zone 82, for removing of any heavy hydrocarbons. Additionally, a dryer 84 such as a knockout drum or vessel with an adsorbent may be utilized for removal of any water from the cleaned regenerant stream 80 to provide a purified regenerant stream 86. The purified regenerant stream 86 may be passed to in various different configurations. For example, the purified regenerant stream 86 may be compressed and recycled back to the dryer zone 50 to be used as the regenerant gas 52. In at least one embodiment, the regenerant gas 52 may comprise a portion of the reactor effluent 28, or a portion of the effluent streams 28a, 28b, 28c, 28d from one of the reactors 18a, 18b, 18c, 18d. In this case, the purified regenerant stream 86 may be combined with one of the effluent streams 28a, 28b, 28c, 28d or passed to product separator 62, for example by being combined with the dryer output stream 58. Alternatively, the purified regenerant stream 86 may be compressed and combined with the compressed effluent 44. As will be appreciated, the order of compression and removal of water and other impurities from the cleaned regenerant stream 80 may be changed from the described embodiments. In at least one embodiment, a regenerant gas is cleaned or further purified by cooling.

In other embodiment of the present invention, spent regenerant gas 54 is cleaned in a cleaning zone 56. The cleaning zone 56 may comprise solid adsorbent configured to selectively adsorb immobilize hydrogen sulfide. The cleaned regenerant gas 80 may be is used in a closed or semi-closed loop in which it is recycled and reused to regenerate the regenerable adsorbent. Make-up or fresh regenerant gas may be added as needed throughout the process. Various contemplated regenerant gases include nitrogen, saturated hydrocarbons, and natural gas.

In sum, by utilizing such a cleaning process for the regenerant gas, the various processes according to the present invention allow for the use of caustic may be eliminated or minimized. As discussed above, the disposable adsorbent addresses the environmental concerns because some adsorbents are easier to dispose of compared to the caustic solution or solid hydroxide pellets. Additionally, the cost of supplying and disposing of the adsorbent is believed to be considerably less than the same costs associated with the caustic solution or solid hydroxide pellets. Finally, some of the processes provide for the recycling of a cleaned regenerant gas to the dryer section as opposed to being used as a fuel gas.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for removing contaminants from a reactor effluent of a catalyst dehydrogenation process, the process comprising:
   dehydrogenating a paraffin feed in a dehydrogenation reaction zone under dehydrogenation reaction conditions in the presence of a dehydrogenation catalyst to form a reactor effluent containing olefins;
   compressing the reactor effluent to provide a compressed effluent;
   removing chloride contaminants from the compressed effluent in a chloride removal zone to provide a treated effluent;
   removing water and hydrogen sulfide from the treated effluent in a dryer zone to provide a dryer output stream including olefins and unconverted paraffins, the dryer zone having at least one vessel comprising a regenerable adsorbent;
   separating the dryer output stream into a vapor stream and a liquid stream comprising an olefin product stream;
   regenerating the regenerable adsorbent in the dryer zone with a regenerant gas stream to produce a spent regenerant stream, the spent regenerant stream including water and hydrogen sulfide; wherein the regenerant gas stream comprises a portion of the reactor effluent;
   removing the hydrogen sulfide from the spent regenerant stream in a regenerant cleaning zone to provide a cleaned regenerant stream, the regenerant cleaning zone including at least two vessels having a sorbent to remove hydrogen sulfide from the spent regenerant stream; wherein two vessels are operated in a lead-lag configuration; wherein at least one vessel is used as a heat exchanger to remove heat from the cleaned regenerant stream to provide a cooled regenerant stream;
   removing contaminants form the cooled regenerant stream; and
   recycling the cooled regenerant stream to provide to the dryer as the regenerant gas stream.

2. The process of claim 1 wherein the dehydrogenation reaction zone comprises a plurality of reactors, and wherein the regenerant gas stream comprises an effluent stream.

3. The process of claim 2 further comprising:
   compressing the cleaned regenerant gas stream to provide a compressed regenerant gas; and
   passing the compressed regenerant gas to a water removal vessel to remove water, heavy hydrocarbons, or both from the compressed regenerant gas.

4. The process of claim 3 further comprising:
   passing the compressed regenerant gas to the product separator.

5. The process of claim 3 further comprising:
   combining the compressed regenerant gas with the compressed effluent.

6. The process of claim 3 further comprising:
   combining the compressed regenerant gas with the treated effluent.

7. The process of claim 1 wherein the sorbent in the regenerant cleaning zone comprises a solid adsorbent which includes metal oxide on a support.

* * * * *